United States Patent [19]

Damodaran et al.

[11] Patent Number: 5,847,089
[45] Date of Patent: Dec. 8, 1998

[54] CARBOXYL-MODIFIED SUPERABSORBENT PROTEIN HYDROGEL

[75] Inventors: Srinivasan Damodaran; Der-Chyan Hwang, both of Madison, Wis.

[73] Assignee: Wisconsin Alumni Research Foundation, Madison, Wis.

[21] Appl. No.: 472,551

[22] Filed: Jun. 7, 1995

[51] Int. Cl.$^6$ ............... C07K 1/10; C08H 1/00; C08H 1/02
[52] U.S. Cl. ............ 530/410; 426/573; 252/315.01; 106/645; 530/354; 530/370; 530/345; 530/402
[58] Field of Search .................. 530/410, 354, 530/370, 345, 402; 106/645; 426/573; 252/315.01

[56] References Cited

U.S. PATENT DOCUMENTS

| | | | |
|---|---|---|---|
| 2,729,628 | 1/1956 | Mann | 260/123.5 |
| 2,923,691 | 2/1960 | Young et al. | 260/6 |
| 3,685,998 | 8/1972 | Miller | 99/2 |
| 3,720,765 | 3/1973 | Miller | 424/177 |
| 4,264,493 | 4/1981 | Battista | 260/117 |
| 4,349,470 | 9/1982 | Battista | 260/117 |
| 4,416,814 | 11/1983 | Battista | 260/117 |
| 4,883,864 | 11/1989 | Scholz | 530/356 |

FOREIGN PATENT DOCUMENTS

| | | |
|---|---|---|
| 1569878 | 6/1980 | United Kingdom . |
| 9403155 | 2/1994 | WIPO . |

OTHER PUBLICATIONS

Noriki et al. (Agric. Biol. Chem) 1985 49:2283–2286.

*Primary Examiner*—Stephen Walsh
*Assistant Examiner*—Michael D. Pak
*Attorney, Agent, or Firm*—DeWitt Ross & Stevens S.C.

[57] ABSTRACT

The present invention is a biodegradable, reversibly-swellable, polyvalent cation-binding, protein-based hydrogel which comprises an acyl-modified protein matrix in which the acyl-modified protein matrix is crosslinked with a bifunctional crosslinking reagent, and a method of making the same.

8 Claims, 10 Drawing Sheets

CARBOXYL-MODIFIED SUPERABSORBENT PROTEIN HYDROGEL

This invention was made with United States government support awarded by the USDA, Grant No. USDA-NRICGP PROJECT #93-37500-9242. The United States government has certain rights in this invention.

FIELD OF THE INVENTION

The present invention relates to protein hydrogels. More specifically, the present invention relates to chemically modified protein hydrogels which are capable of absorbing a large amount of water or other liquid per unit mass.

DESCRIPTION OF THE PRIOR ART

Beginning in the early 1970's, and continuing to the present day, there has been a growing awareness that the continued widespread use of non-biodegradable, petroleum-based polymeric materials may pose serious environmental concerns. These concerns are heightened by production statistics showing the enormous and still-growing volume of non-biodegradable plastics produced annually, the vast majority of which are ultimately interred in landfills. This raises concerns not only as to the amount of space available for solid waste disposal (which is disappearing at an increasingly rapid pace), but also raises equally serious concerns that the leaching of toxic monomers and oligomers from landfilled plastics will contaminate ground water, thereby causing health problems in humans and animals.

In addition to concerns regarding human health and the environment, the world-wide depletion of petroleum reserves, in combination with wildly fluctuating petroleum prices due to political and economic conflicts, indicates that less dependence on petroleum-derived products might be prudent. Therefore, the development of alternative, and renewable, resources for industrial products is needed.

Because of the factual and/or perceived economic, environmental, and public health concerns accompanying non-biodegradable, petroleum-based products, a non-petroleum-based, environmentally safe, biodegradable, and renewable source for industrial products is needed. As evidenced by the following references, several types of useful products have been fabricated from renewable sources of starting materials.

For instance, Mann, U.S. Pat. No. 2,729,628, describes a process for increasing the intrinsic viscosity of a long chain polypeptide, particularly natural proteins such as peanut protein, soybean protein, casein, egg albumin, and blood albumin by acylating the protein with terephthalyl dichloride. Here, the protein is reacted with the terephthalyl dichloride using the Schotten-Baumann method at a temperature of from about 0° to 30° C.

Young et al., U.S. Pat. No. 2,923,691, describe the polymerization of animal proteins to improve their characteristics for use as animal glue. Young et al. introduce aldehydes to an animal glue protein so as to modify the viscosity and jelly characteristics of the glue product without solidifying or insolubilizing the protein. Here, Young et al. are interested in increasing the viscosity and jelly strength of last run animal glues, which tend to be of inferior quality. The process described by Young et al. includes two steps: first, a cyanic acid salt is reacted with the protein material; second, an aldehyde, such as formaldehyde or glucose, is added to the protein material.

Two patents to Miller (U.S. Pat. Nos. 3,685,998 and 3,720,765), and assigned to the Monsanto Company, describe improved protein feed materials for ruminants. In the Miller patents, protein feeds are rendered resistant to digestive breakdown in the rumen, but not in the abomasum and intestines, by treating protein-containing feed material with a polymerized unsaturated carboxylic acid or anhydride. For instance, the proteinaceous feedstuff is treated with a polyanhydride such as poly(maleic anhydride). This renders the protein feedstuff substantially indigestible in the fluid medium of the rumen, yet still digestible in the acidic media of the abomasum and the intestines. In this manner the proteins of the feedstuff are spared breakdown in the rumen, and are available for absorption in the subsequent digestive organs.

Three patent references to Battista (U.S. Pat. Nos. 4,264,493; 4,349,470; and 4,416,814) describe the formation of protein hydrogel structures formed from natural proteins having molecular weights not exceeding 100,000 by dissolving the protein in an aqueous acidic solution, crosslinking the protein, and air drying the solution to a moisture content not exceeding 10 percent. The Battista patents are largely drawn to the formation of clear products such as soft contact lenses, ophthalmological films, and the like.

Although Battista refers to the compositions described therein as hydrogels, that term is defined within the Battista references as meaning "a cross-linked protein polymer of natural origin having an average molecular weight of about 100,000 or less, capable of being swollen by water over a wide range of water contents ranging from as low as 30 percent to 1,000 percent and higher while possessing useful rheological control properties for a specific end product uses." (See for instance, U.S. Pat. No. 4,264,493, column 1, lines 1914 27.) The hydrogels described by Battista are not designed to be superabsorbent. Rather, they are designed to be optically clear and to have sufficient mechanical integrity to function as soft contact lenses.

The protein hydrogel structures described in the Battista patents are made from natural protein raw materials that form clear solutions in water. The protein raw material is first dissolved in an acidic aqueous solution of from pH 3.5 to about pH 5.5. A crosslinking agent is then added to the acidic protein solution. Battista's preferred crosslinking agent is Formalin (37% formaldehyde); however, Battista describes other suitable crosslinking agents which may be used, including glutaraldehyde. It must be noted, however, that the Battista patents do not describe acyl-modification of the protein starting material. Nor do the Battista patents describe a superabsorbent protein hydrogel. The protein hydrogels described in the Battista references are designed to have increased wet strength capabilities, thereby enabling their use in soft contact lenses.

Many disadvantages which accompany synthetic hydrogels (such as non-biodegradability) can be overcome by using hydrogels derived from natural polymer sources. In addition to chemically-crosslinked protein hydrogels, such as those described by Battista, many proteins can be thermally induced to form gels. The most critical requirements for any type of biopolymer hydrogel are that the gel should have the capacity to absorb a large amount of water relative to its mass upon rehydration, and that the gel material itself should resist dissolution.

However, conventional thermally-induced protein hydrogels do not swell to their original gel volume after they have been dehydrated. This decreased swelling capacity is related to increased hydrogen bonding, as well as electrostatic and hydrophobic interactions which occur in the dehydrated protein. The loss of swelling of thermally-induced protein hydrogels limits their range of industrial applicability.

In view of this, there is a clear need for a protein-based hydrogel which is highly absorbent, biodegradable, and reversibly swellable. The present invention provides such a protein hydrogel.

Perhaps the most desirable of renewable production materials is agricultural biomass. This is due, in large part, to the tremendous amount and variety of agricultural products which are produced in the United States. For instance, biomass (mainly maize) is currently used to produce ethanol for fuel. Fibrous biomass is widely used in the paper and forest products industry. Starch-derived products are also widely utilized in various industrial applications, such as the packing industry, in addition to their use in the food industry.

However, among biopolymers, proteins are perhaps the most under-utilized and under-rated in terms of their industrial applications. They are primarily regarded solely as functional and nutritional ingredients in foodstuffs. Their enormous potential as structural elements in non-food industrial applications is largely unrecognized and unrealized. This is unfortunate because proteins offer several distinct advantages over more conventional types of biomass.

For example, unlike polyol-based natural polymers, such as cellulose and other carbohydrates, proteins contain several reactive side groups, including amino, hydroxyl, sulfhydryl, phenolic, and carboxyl moieties. These reactive groups can be used as sites of chemical modification and crosslinking to produce novel polymeric structures. The present invention relates to such a novel polymeric structure: a protein-based, biodegradable, superabsorbent hydrogel.

As a generic class of polymers, hydrogels of all types find high volume uses in industrial applications, consumer products, and environmental applications. Such applications include diapers, catamenial devices, and industrial absorbents. As used herein, the unqualified term "hydrogel" refers to any naturally-occurring or synthetic material which exhibits the ability to swell in water or some other liquid and to retain a significant fraction of liquid within its structure, but which will not dissolve in the liquid.

Several synthetic hydrogel materials are currently in use. These include such synthetic hydrogels as poly(hydroxyalkyl methacrylates), polyacrylate, poly(acrylamide), poly(methacrylamide) and derivatives thereof, poly(N-vinyl-2-pyrolidone), and poly(vinylalcohol). While these synthetic hydrogel polymers exhibit several interesting properties, their use in industrial, consumer, and environmental applications is less than desirable because of the toxicity of residual monomers and oligomers which are normally present in these gels. Moreover, the poor biodegradability of these synthetic hydrogels also poses the long-term environmental concerns discussed above.

Clearly then, there exists the need for a biodegradable, superabsorbent, biomass-derived hydrogel which exhibits reversible swelling.

SUMMARY OF THE INVENTION

In view of the above discussion, it is a principal aim of the present invention to provide a protein-based hydrogel which is superabsorbent, reversibly swellable, biodegradable, and capable of binding divalent cations.

A further aim of the invention is to provide a protein-based hydrogel which can be formed from a wide range of protein starting materials, and which can be used as a substitute for wholly synthetic hydrogels.

In its simplest embodiment, the present invention relates to a protein-based hydrogel which comprises an acyl-modified protein matrix which has been crosslinked with a bifunctional crosslinking reagent.

More specifically, the present invention includes a protein-based hydrogel which comprises a soy protein isolate which has been acyl-modified by treatment with ethylenediaminetetraacetic acid dianhydride to yield an acyl-modified protein matrix. The acyl-modified protein matrix is then crosslinked with glutaraldehyde to yield a biodegradable, superabsorbent, protein-based hydrogel.

The protein hydrogels of the present invention are capable of absorbing more than 100 times their dry weight in water. They are also capable of sequestering divalent cations.

The present invention also includes a method of making the protein-based hydrogel described immediately above. The method includes the steps of treating a protein with an acylating agent to yield an acyl-modified protein matrix, and crosslinking the acyl-modified protein matrix with a bifunctional crosslinking agent to yield the protein hydrogel.

In more detail, the present invention includes a method of making a protein-based hydrogel which includes the steps of dissociating and/or unfolding protein molecules within an aqueous protein solution by application of heat, and then adding an acylating agent to the protein solution to yield an acyl-modified protein. The acyl-modified protein is then crosslinked by addition of a bifunctional crosslinking agent.

The present invention is a protein hydrogel having the above-described properties. The protein from which the protein hydrogel is derived can be from any plant or animal source, without limitation. A preferred protein source, its preference derived in large part from its abundance and low cost, is soy-derived protein.

The protein hydrogel of the present invention is made by first chemically modifying lysyl residues of a protein by the addition of one or more carboxyl moieties thereto. Preferably, this is done by acylation of the lysyl residues with a polycarboxylic acid anhydride. This is followed by crosslinking of the protein chains with a bifunctional crosslinking agent to yield a protein hydrogel that exhibits superabsorbent, pH-sensitive and ionic strength-sensitive reversible swelling.

The protein hydrogel of the present invention also strongly binds divalent cations. This enables the protein hydrogel to function as a cationic sequestering agent. The protein hydrogel can be used to remove divalent metal cations and organic cations from ground water, effluent liquid waste streams, and the like.

In operation, the protein hydrogel can be used wherever high absorption of liquid, or sequestering of divalent cations is desired. Potential end uses for the protein hydrogel include diapers, tampons and menstrual pads, industrial absorbents, spill dams and sealers, ground and waste water reclamation applications, heavy metal sequestration, and the like.

DETAILED DESCRIPTION OF THE INVENTION

Figure 1:
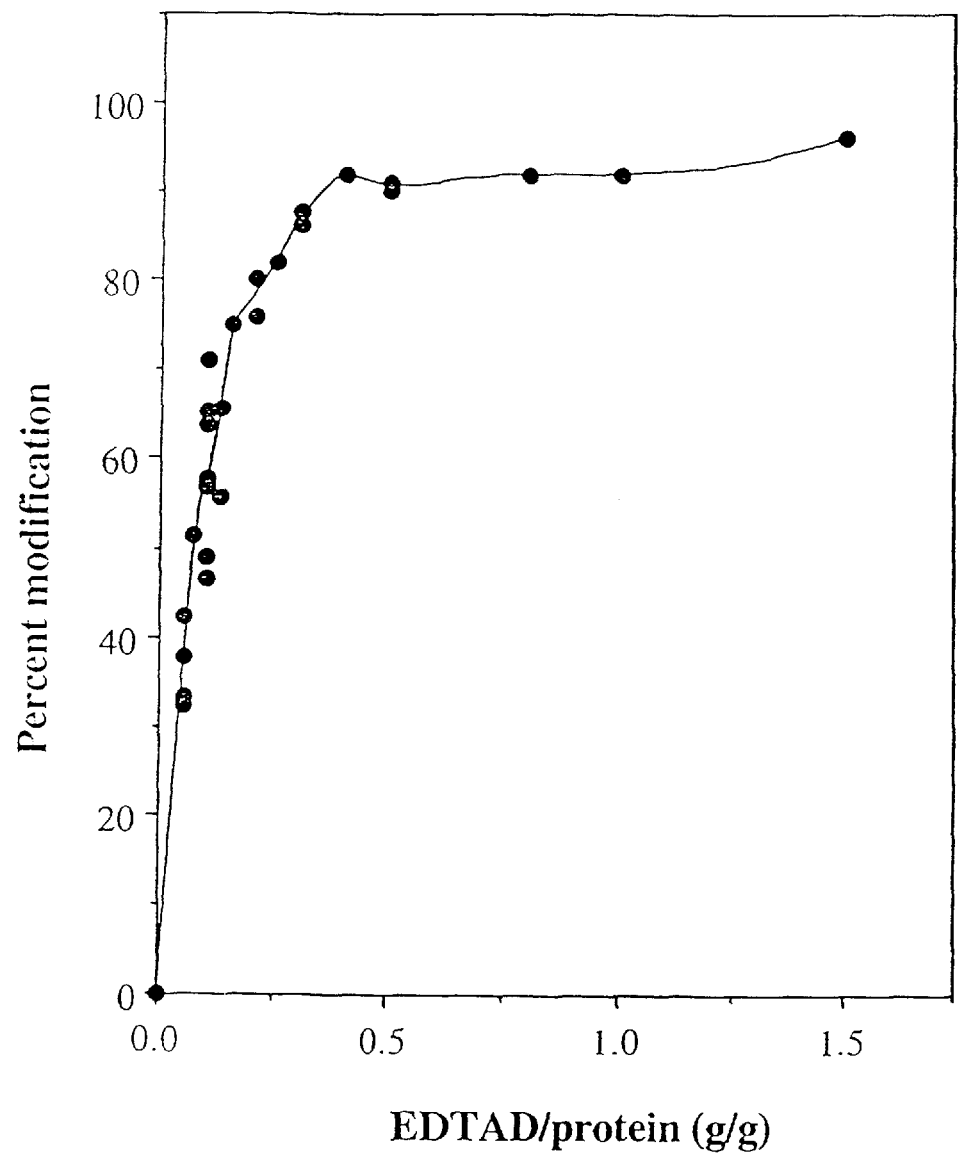
FIG. 1 is a graph showing the effect of the ratio of EDTAD to SPI (g/g) on the extent of modification of lysine residues within SPI. Here, a 1% SPI solution was heated for 30 minutes at 65° C. and pH 12, cooled to room temperature, and then modified at room temperature at pH 12.

At the heart of the present invention is chemical modification of a protein so as to first introduce carboxyl moieties into the n-butylamino side groups of lysine residues within the protein. The modified protein molecules are then crosslinked using a bifunctional crosslinking agent to yield a biodegradable, superabsorbent, protein hydrogel.

As noted above, the protein starting material can be selected from any source, animal, vegetable, or microbial, without limitation. For instance, while soy protein is preferred due to its low cost, the protein hydrogel described herein can be manufactured from other oilseed proteins, leaf proteins (e.g. alfalfa), microbial proteins, animal proteins, and proteins recovered from food processing wastes. Crude protein concentrates, as well as protein isolates will function equally well in the present invention. And, since the protein hydrogel is not generally intended for consumption, the starting material need not be of food grade.

The preferred protein source is defatted soy beans, which are extracted with water to yield a soy protein isolate. Generally, the soy beans are crushed to meal (defatted soy flour can be purchased commercially), and then extracted with copious quantities of water. Extraction is accomplished by conventional means using any type of suitable equipment (mixers, agitators, separatory funnels, etc.). Extraction may be carried out in a continuous process, or batchwise.

The extract is then treated to isolate the protein. This can be accomplished in any suitable fashion. For instance, this can be accomplished by treatment with acid to precipitate the proteins dissolved within the extract to yield soy protein isolate. The protein will normally precipitate from solution at about pH 4.5 The soy protein isolate (SPI) may be optionally dialyzed or further purified (e.g., by recrystallization) if desired. Other isolation methods, such as evaporation of the solvent, or chromatography, can be used with equal success. While the present invention may be practiced with any type of protein, for brevity and clarity only, the remainder of the specification shall be limited to protein hydrogels made using the above-described SPI.

The SPI is then modified with a carboxylic group-containing acylating agent. The acylating agent reacts with n-butylamino groups of lysine residues within the SPI, and functions to introduce carboxyl moieties into the SPI. Preferably, the acylating agent is a polycarboxylic anhydride, a mono-anhydride, a dianhydride, or a combination thereof. As used herein, the term "anhydride" shall mean any of the preceding types of anhydrides. Suitable dianhydrides which can be used in the present invention include, for example, benzenetetracarboxylic dianhydride, cyclobutane tetracarboxylic dianhydride, diethylene-triamine-pentaacetic dianhydride, and ethylenediaminetetraacetic acid dianhydride (EDTAD). EDTAD is the preferred acylating agent. Again, for brevity, the description which follows will be limited to addition of EDTAD to the SPI. This is for brevity and clarity only, and is understood not to limit the invention claimed herein in any fashion.

Introduction of the EDTAD into the SPI is performed by step-wise addition of solid EDTAD to an aqueous solution of SPI. It must be remembered, however, that EDTAD is a bifunctional reagent which is capable of cross-linking polypeptides either inter- or intramolecularly. Two possible reaction pathways for the reaction of EDTAD with a protein are shown below:

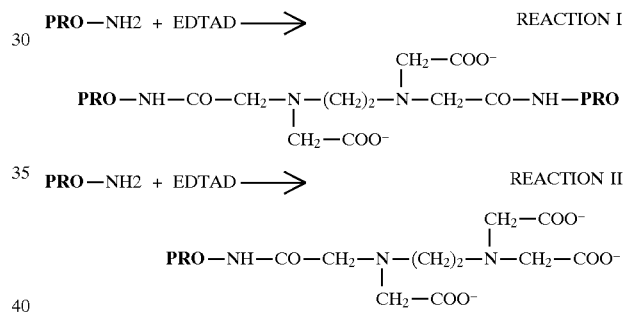

wherein PRO is the protein being modified.

In Reaction I, one molecule of EDTAD reacts with two lysyl residues to form a linkage. When the reaction of the protein with EDTAD proceeds by Reaction I, the result is the incorporation of only one carboxyl moiety per lysyl residue. Moreover, if Reaction I occurs between subunits of a protein molecule, the intramolecular crosslinking may impair swelling of the modified protein.

In Reaction II, one molecule of EDTAD reacts with one lysyl residue and one water molecule. In this reaction, three carboxyl moieties per lysyl residue are incorporated into the protein, and no linkages are formed. This greatly increases the net anionic charge of the modified protein, which aids in unfolding the protein structure. Because no linkages are formed, the swellability of the modified protein is not impaired.

In light of the bifunctionality of EDTAD, in order to form a protein hydrogel having maximum absorbency, EDTAD should be added to the SPI under conditions which favor Reaction II over Reaction I. Conditions which favor Reaction II over Reaction I are those conditions wherein the protein is present in dilute solution, and the individual protein molecules are partially dissociated and/or denatured, thereby lessening the possibility of EDTAD reacting with two protein molecules. The reaction can be carried out at a temperature range of from about 5° C. to about 100° C. It is preferred that the reaction be conducted at mildly elevated temperatures, from ambient to about 100° C., under basic conditions, about pH 8 to pH 12. However, the reaction conditions should not be so rigorous as to cause hydrolytic degradation of the protein chains.

The preferred reaction protocol to optimize reaction of the protein by the mechanism of Reaction II is to first incubate the SPI in a dilute aqueous solution of about pH 8 to pH 12, at a mildly elevated temperature of about 65° C. Most preferably, the pH of the solution should approach 12. However, care must be taken not to exceed about pH 12. If the alkalinity of the solution rises above approximately pH 12, the protein may suffer extensive alkaline hydrolysis. The concentration of SPI in the solution should be on the order of about 1 to 2%. The SPI should be incubated for approximately 30 minutes at 65° C. Longer incubations times are acceptable so long as alkaline hydrolysis does not occur. The incubation period serves to dissociate and/or denature the protein molecules of the SPI.

The incubation may also be performed under acidic conditions, down to about pH 2. However, since the preferred acylation reaction takes place in alkaline solution, it is preferred that the incubation is also done under alkaline conditions so as to minimize salt formation during the acylation reaction.

After incubation, the solution is allowed to return to room temperature, and solid EDTAD is added slowly thereto, over a period of one to three hours. The reaction should be carried within a pH range of from about 8 to 12. It is preferred that the pH of the reaction be held constant during acylation by the addition of base, preferably NaOH. This can be done automatically using a commercially-available pH-Stat apparatus (Fisher Scientific). Under these conditions, little or no alkaline hydrolysis of the SPI occurs.

Of course, the reaction conditions can be easily adjusted by one of skill in the art such that Reaction I prevails. For instance, a shortened incubation period, or omission of the incubation step entirely will tend to favor Reaction I, as will adding the EDTAD to a more concentrated SPI solution. Performing the acylation at an alkalinity closer to pH 9 tends to favor the Reaction I pathway over the Reaction II pathway.

Adjusting the relative rates of the two reactions will change the characteristics of the final protein hydrogel. While optimization of Reaction II yields a protein hydrogel having superior swellability and greater overall anionic charge, optimization of Reaction I yields a stiffer, less absorbent hydrogel, which is desirable in some applications. Knowledge of the interplay between the two reactions allows the physical characteristics of the final gel product to be tailored to fit a wide variety of final applications.

The ratio of reaction by the Reaction I pathway versus the Reaction II pathway can be determined by electrometric titration of various modified and unmodified SPI samples. The titration curves of the modified samples are then compared to unmodified samples subjected to the same reaction conditions. The number of carboxyl groups per $10^5$ gmole of protein is calculated from the number of moles of H+ion dissociated (or, by the number of moles of NaOH consumed) by the protein during titration from pH 2.0 to the isoionic point of the protein. Titration curves for native SPI, and SPI subjected to pH 12 and 65° C. are essentially identical (data not shown), illustrating that heat treatment at pH 12 does not result in deamidation of the glutamine and asparagine residues of SPI. Knowing this, any increase in the carboxyl group content of SPI modified under these conditions must be due to incorporation of EDTAD at the lysyl residues of the SPI.

Figure 2:
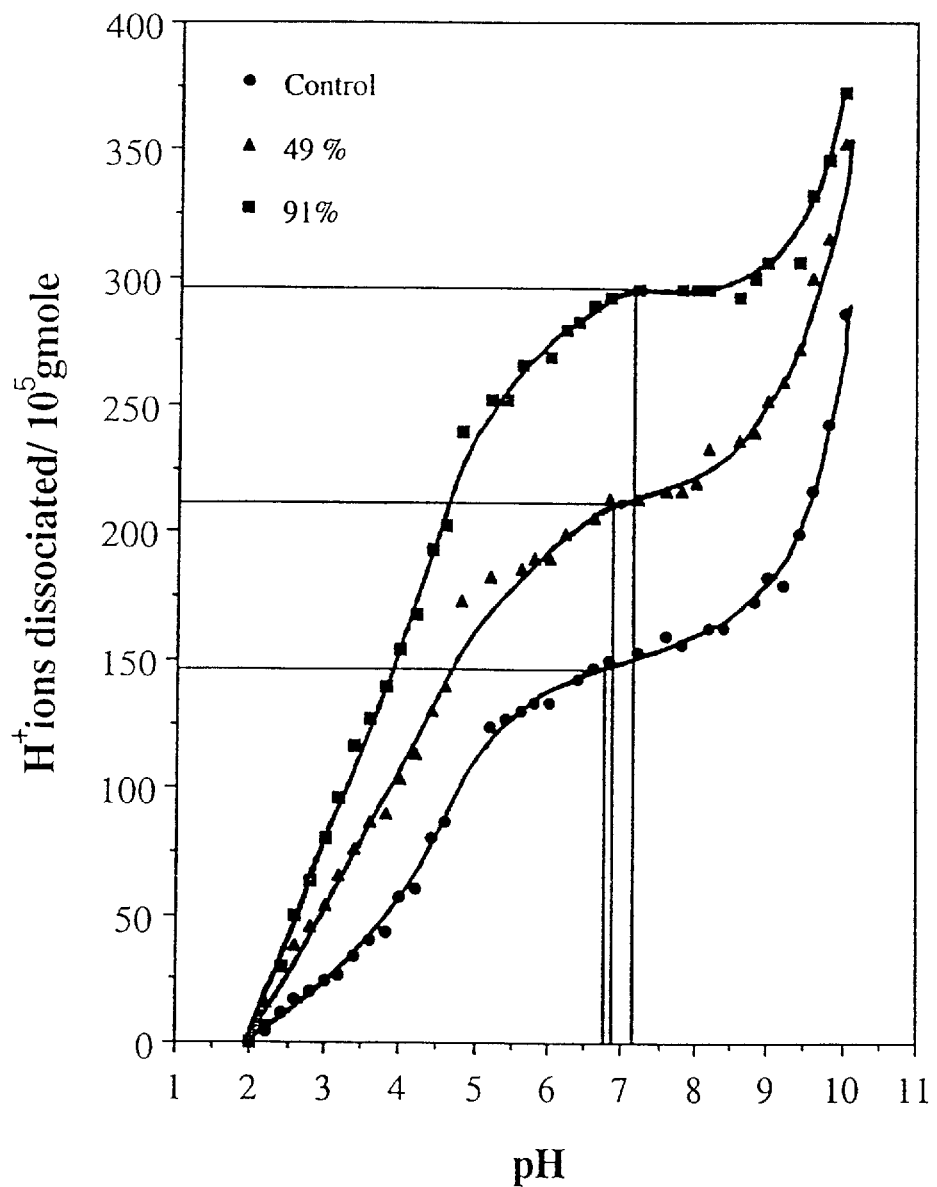
FIG. 2 is an electrometric titration curve for modified and unmodified soy protein isolates. ■ is the curve for 91% EDTAD-modified SPI, ▲ is the curve for 49% EDTAD-modified SPI, and ● is the curve for unmodified SPI.

An illustrative electrometric titrimetric plot is shown in FIG. 2. Here, ■ is the curve for 91% EDTAD-modified SPI, ▲ is the curve for 49% EDTAD-modified SPI, and ● is the curve for unmodified SPI. The hydrogels used in this plot were modified according to the above protocol. The perpendicular intersecting lines indicate the isoionic point for each curve.

The extent of acylation can be varied so as to modulate the physical characteristics of the final gel product. This can be done quite easily by varying the ratio of protein to added EDTAD (or other acylating agent). The greater the amount of EDTAD added per unit protein, the greater the extent of modification. FIG. 1 shows a plot of the percent of lysine residues within SPI which are acylated at a given ratio of EDTAD to SPI (g/g). For instance, at 0.5 grams of EDTAD per gram of SPI, approximately 90% of the lysine residues of SPI have been modified. These ratios will, of course, vary depending on the nature of the starting protein. Factors such as whether the protein is a single chain or formed from several sub-chains will have an effect on the extent of modification. Extent of modification is expressed herein as the percentage of available lysine residues which have been acylated.

It must also be remembered that the crosslinking step, described in full below, also utilizes lysine residues within the protein to crosslink the protein chains. Therefore, it is preferred that the extent of modification not exceed 98% of available lysine residues. This maximum extent of modification should also be decreased if the starting protein is particularly low in lysine residues. In order to obtain the advantages of increased carboxyl moiety content, it is preferred that a minimum of 50% of the lysine residues of the starting protein be acyl modified.

Figure 3:
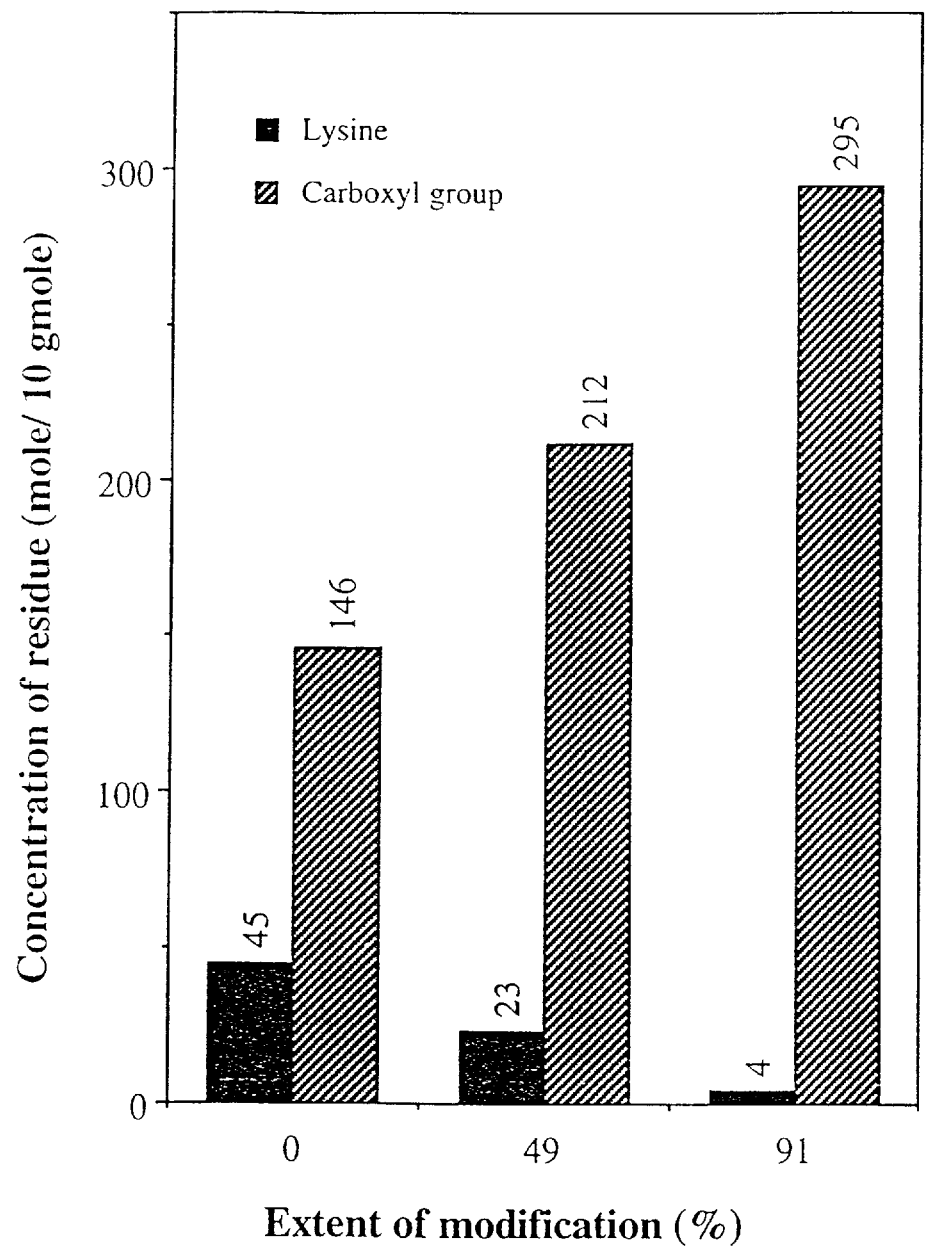
FIG. 3 is a graph depicting the relationship between the number of lysine residues and the carboxyl group content of EDTAD-modified SPI as a function of the extent of modification.

FIG. 3 shows the relationship between the number of lysine residues and the carboxyl group content of EDTAD-modified SPI as a function of the extent of modification for SPI modified according to the above-described preferred protocol. Here, native SPI, shown in the left-hand plot, has about 146 carboxyl groups and 45 lysine residues per $10^5$ gmoles (approximately 870 total amino acid residues) of SPI. The 49% EDTAD-modified SPI (middle plot) is found to contain 212 carboxyl groups and 23 lysine residues, while the 91% EDTAD-modified SPI is found to contain about 295 carboxyl groups and 4 lysine residue per $10^5$ gmole SPI. FIG. 3 shows that for each lysine residue modified as described above, an average of 2.3 carboxyl groups are incorporated into the protein. This confirms that, under the preferred reaction protocol, reaction of SPI with EDTAD predominantly follows the Reaction II pathway.

After acylation, the protein solution is exhaustively dialyzed against deionized water to remove salts (in this case, primarily sodium EDTA) formed in the reaction. The dialyzed modified protein may be optionally lyophilized to yield an acyl-modified protein.

EDTAD is the preferred acylating agent because, inter alia, it is essentially non-toxic. The only reactive groups introduced into the protein by the addition of EDTAD are the carboxyl groups. When added to the SPI according to the protocol described above, any unreacted EDTAD will readily react with water and NaOH, to be converted into sodium ethylenediaminetetraacetic acid (EDTA). Since sodium EDTA is a "Generally Regarded As Safe" (GRAS) food additive, there is no concern in regard to the toxicity or environmental safety of any residual amount of sodium EDTA (if any) remaining in the modified protein. Unlike poly(acrylate) or poly(acrylamide)-based hydrogels, which may contain residual monomers which are toxic, the present protein hydrogel, if it contains any residual reagents, would only contain residual sodium EDTA.

While not being limited to any particular mode of operation, it is believed that the EDTAD acylating agent, by reaction with the lysyl residues of the protein, causes extensive unfolding of the protein molecules via intramolecular electrostatic repulsion caused by the carboxylic acid substituents on the acylating agent. This is believed to convert the rigid, globular structure of soy globulins into a random-coil-type, polyanionic polymer. The substantial polyanionic character which the carboxylic acid moieties impart to the SPI are believed to provide numerous sites for water binding.

Figure 4:
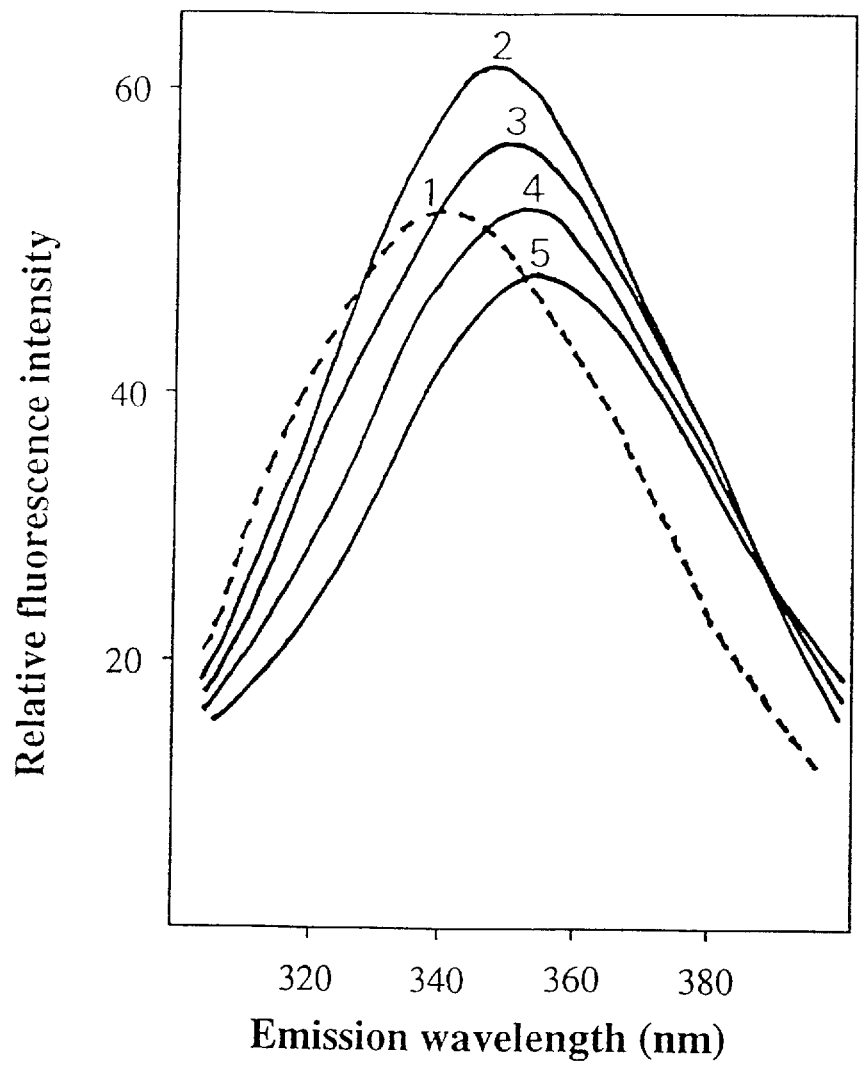
FIG. 4 is a fluorescent spectrum of native SPI (dotted line, plot 1), and EDTAD-modified SPI showing the unfolding of the protein structure upon incorporation of EDTAD. (2) unmodified SPI, (3) 38% EDTAD-modified SPI, (4) 58% EDTAD-modified SPI, (5) 90% EDTAD-modified SPI.

Evidence of the unfolding of the soy globulins is provided by fluorescent spectroscopy. FIG. 4 is an emission spectra of native SPI ((1), dotted line), unmodified SPI subjected to 65° C. and pH 12 (2), and three EDTAD-modified SPI's of increasing percent modification (curves (3), (4), and (5), respectively). The emission spectrum of native SPI, shown by the dotted line, has a maximum fluorescence intensity at 340.8 nm. The maximum fluorescence intensity ($\lambda_{max}$) of unmodified SPI subjected to the reaction conditions of the preferred protocol (65° C., pH 12, curve (2)) shifted to 343.8 nm, and showed a markedly increased intensity relative to the native SPI. This indicates that denaturation/dissociation of the protein is caused by the incubation conditions, prior to addition of EDTAD. Upon modification with EDTAD, the $\lambda_{max}$ of fluorescence emission shows a shift to longer wavelengths (a red shift) and a decrease in fluorescence intensity. The greater the extent of modification with EDTAD, the greater the red shift, and the greater the decrease in fluorescence intensity (curves (3), (4), and (5)). These changes in fluorescence intensity indicate that tryptophan residues within the SPI are increasingly exposed to solvent due to unfolding of the protein upon modification with EDTAD.

After acylation, the dialyzed and optionally lyophilized modified SPI is crosslinked using a bifunctional crosslinking reagent. A wide variety of suitable bifunctional crosslinking agents are known in the art. Dialdehydes, for instance, like dianhydrides, will also react with lysine residues to form crosslinks between polypeptide chains. Bifunctional aldehydes are excellent crosslinking reagents. In the present invention, any type of dialdehyde, without limitation, can function as a crosslinking reagent. The preferred bifunctional crosslinking reagent is a bifunctional aldehyde having the formula

wherein X is an integer of from 2 to 8. The preferred bifunctional aldehyde from within this small group of homologs is glutaraldehyde (X equals 3).

Crosslinking is preferably carried out in aqueous solution. Here, in order to maximize crosslinking (both intra and intermolecular linkages), a relatively concentrated protein solution is used, and the pH maintained at about pH 7 to pH 10. For instance, to a 15% aqueous solution of acylated SPI at pH 9.0 is added a suitable amount of a 25% aqueous solution of glutaraldehyde. For example, about 150 μl of the 25% glutaraldehyde solution would be added to 10 ml of the 15% protein solution.

The mixture is then thoroughly stirred, and cured overnight at room temperature. The cured gel is then air dried in an oven at 40° C.

The residual amount of glutaraldehyde (if any) contained within the product protein hydrogel can be controlled by careful analysis of the available lysine residues in the modified SPI. By optimizing the ratio of glutaraldehyde to available lysine residues, any residual amount of glutaraldehyde can be minimized, or the residual amount can be eliminated entirely. Also, if a residual amount of glutaraldehyde is found to be present, the effects of the glutaraldehyde can be neutralized by treating the protein hydrogel with low molecular weight amino compounds such as ethanolamine or glycine.

Table 1 is a tabulation of the water uptake capacities of various EDTAD-modified protein hydrogels based upon the extent of EDTAD modification. The values for the amount of water retained in the first four gels represents the amount of water retained within gels made at pH 12 and 65° C. after centrifugation at 214×g. As noted in the table, at 66% modification, 1 gram of the protein hydrogel of the present invention is capable of absorbing over 100 grams of water. In other words, at 66% modification, the present hydrogel is capable of absorbing over 10,000% of its weight in water.

TABLE I

Water Uptake Capacities of Ethylenediaminetetraacetic Dianhydride-Modified Soy Protein Hydrogel[b]

| % Modification | Water Uptake (g water/g dry gel)* |
|---|---|
| 0 | 6.3 + 0.4[a] |
| 32 | 55.5 + 6.1 |
| 47 | 76.5 + 4.7 |
| 66 | 105.6 + 4.0 |

*Represents water retained by the swollen gel at 214 x g.
[a]Values represent mean ± standard error (n = 3).
[b]Gels were made by crosslinking a 15% EDTAD-modified SPI with glutaraldehyde.

Figure 5:
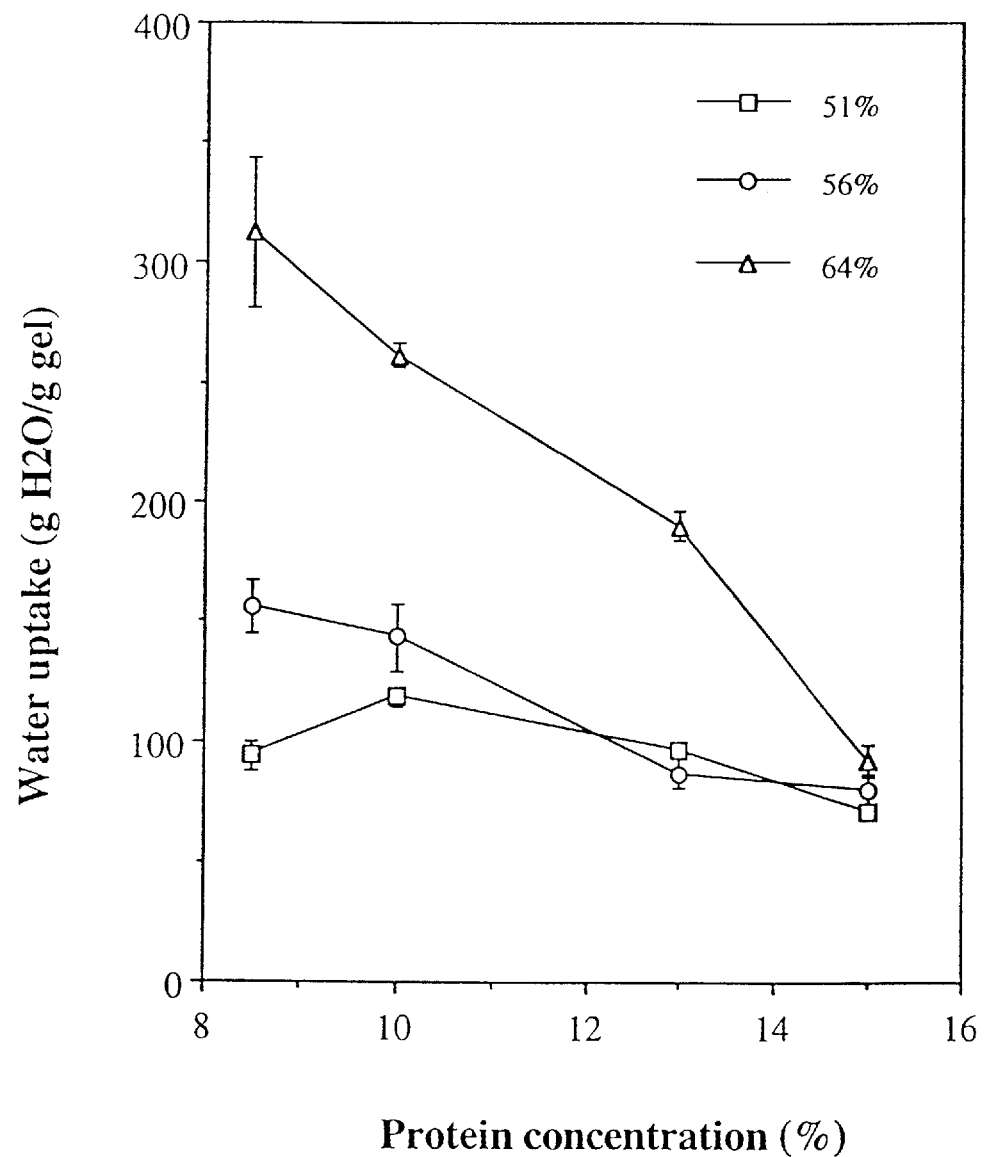
FIG. 5 is a graph showing the effect of protein concentration during the glutaraldehyde crosslinking on water uptake capacities of EDTAD-modified soy protein hydrogels. □ 51% EDTAD-modified SPI, ○ 56% EDTAD-modified SPI, Δ 64% EDTAD-modified SPI.

Several factors influence the ability of the present protein hydrogels to take up water. For example, FIG. 5 depicts water uptake capacities as a function of protein concentration during crosslinking. The water uptake capacity of a 66% EDTAD-modified hydrogel, crosslinked in an 8.5% (w/v) solution is about 300 grams of water per gram of dry gel. In contrast, water absorption decreased to about 120 grams of water per gram of dry gel when the same 66% EDTAD-modified soy protein was cross linked in a 15% solution. This knowledge can be used to create hydrogels with varying water uptake capacities simply by manipulating the protein concentration in the crosslinking step.

Figure 6:
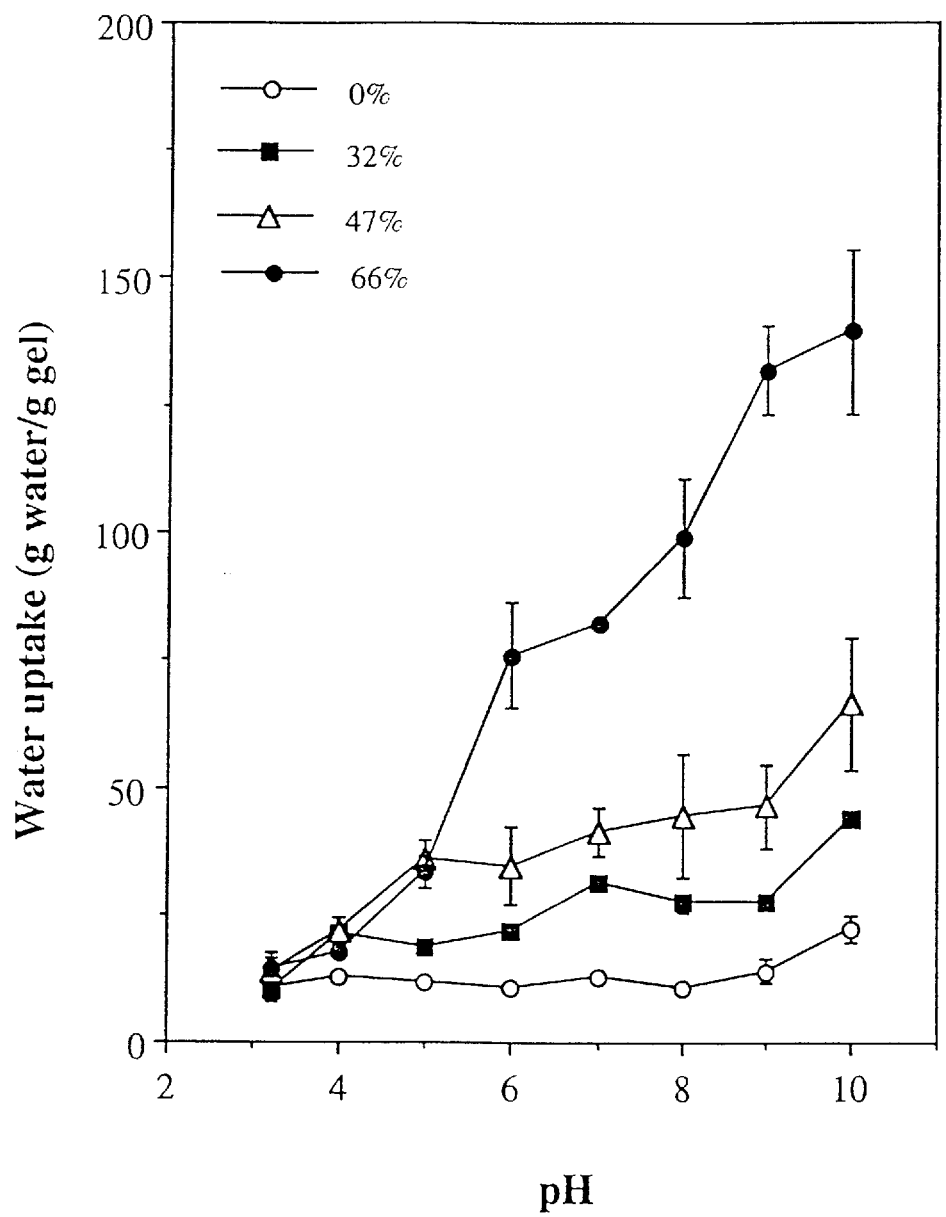
FIG. 6 is a graph showing the effect of pH on water uptake capacities of EDTAD-modified SPI hydrogels. ○ unmodified SPI, ■ 32% EDTAD-modified SPI, Δ 47% EDTAD-modified SPI, ● 66% EDTAD-modified SPI.

Water uptake of the present hydrogels is also pH sensitive. FIG. 6 shows that the higher the alkalinity of the water, the greater the water uptake. For SPI-derived hydrogels, this was true for 32%, 47%, and 66% EDTAD-modified gels.

Figure 7:
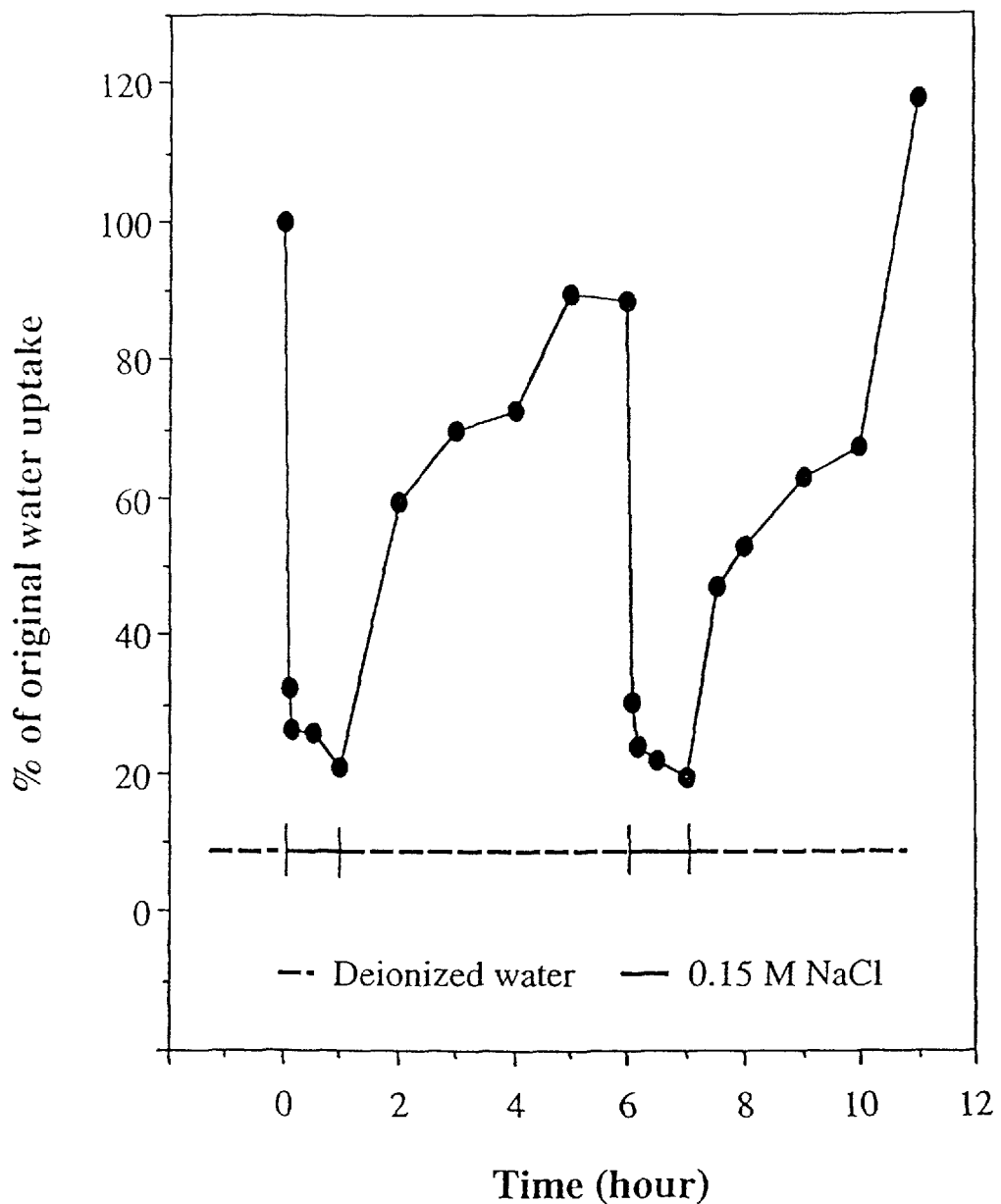
FIG. 7 is a graph showing the reversible water uptake and release properties of a 66% EDTAD-modified SPI hydrogel in response to sequential exposure to deionized water and 0.15M NaCl.

FIG. 7 shows that the protein hydrogels of the present invention are also sensitive to the ionic strength of the water. Fully reversible swelling and shrinkage of the present hydrogels occurs as the gel is cycled between deionized water and a 0.15 NaCl solution.

Figure 8:
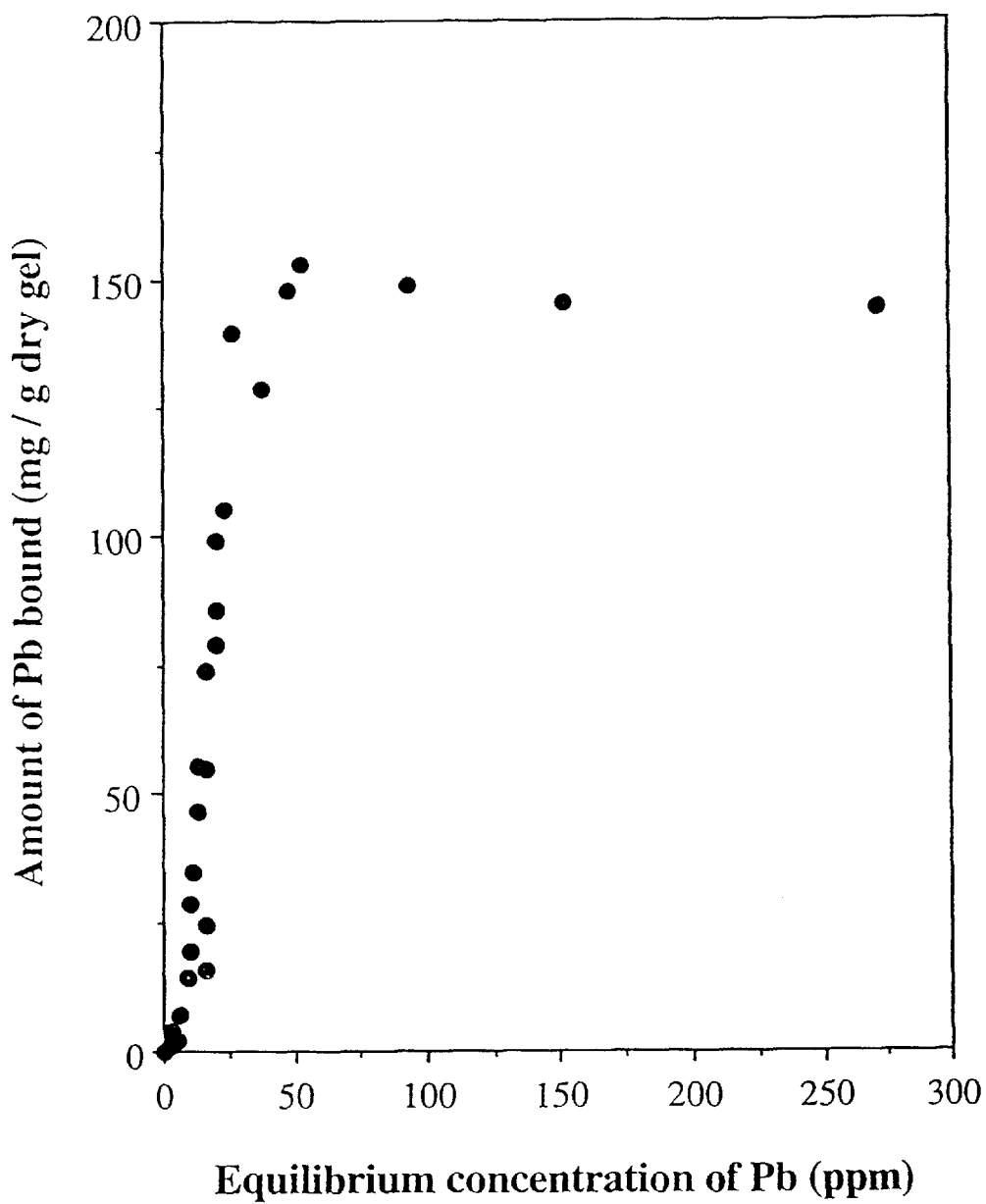
FIG. 8 is a graph showing the Pb$^{++}$binding/chelating properties of a 66% EDTAD-modified SPI hydrogel at 25° C.
Figure 9:
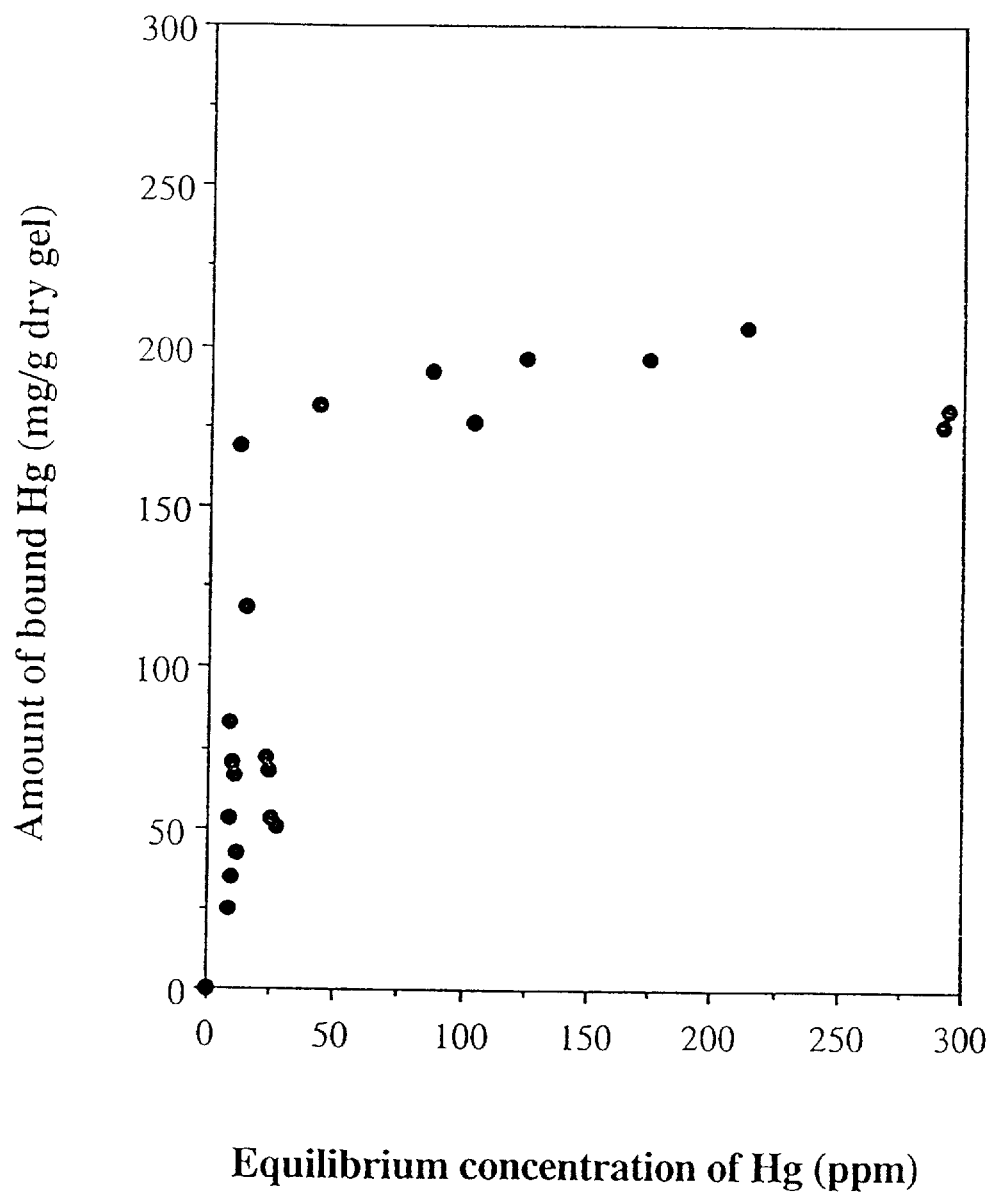
FIG. 9 is a graph showing the Hg$^{++}$binding/chelating properties of a 66% EDTAD-modified SPI hydrogel at 25° C.

FIGS. 8 and 9 further show that the hydrogels of the present invention are capable of chelating divalent heavy metal cations. FIG. 8 shows that, under equilibrium conditions, an EDTAD-modified, glutaraldehyde crosslinked hydrogel is capable of binding approximately 150 mg of $Pb^{++}$ per gram of dry gel. FIG. 9 is an identical plot for mercury. Under equilibrium conditions, the same hydrogel is capable of binding approximately 200 mg of $Hg^{++}$ per gram of dry gel.

Figure 10:
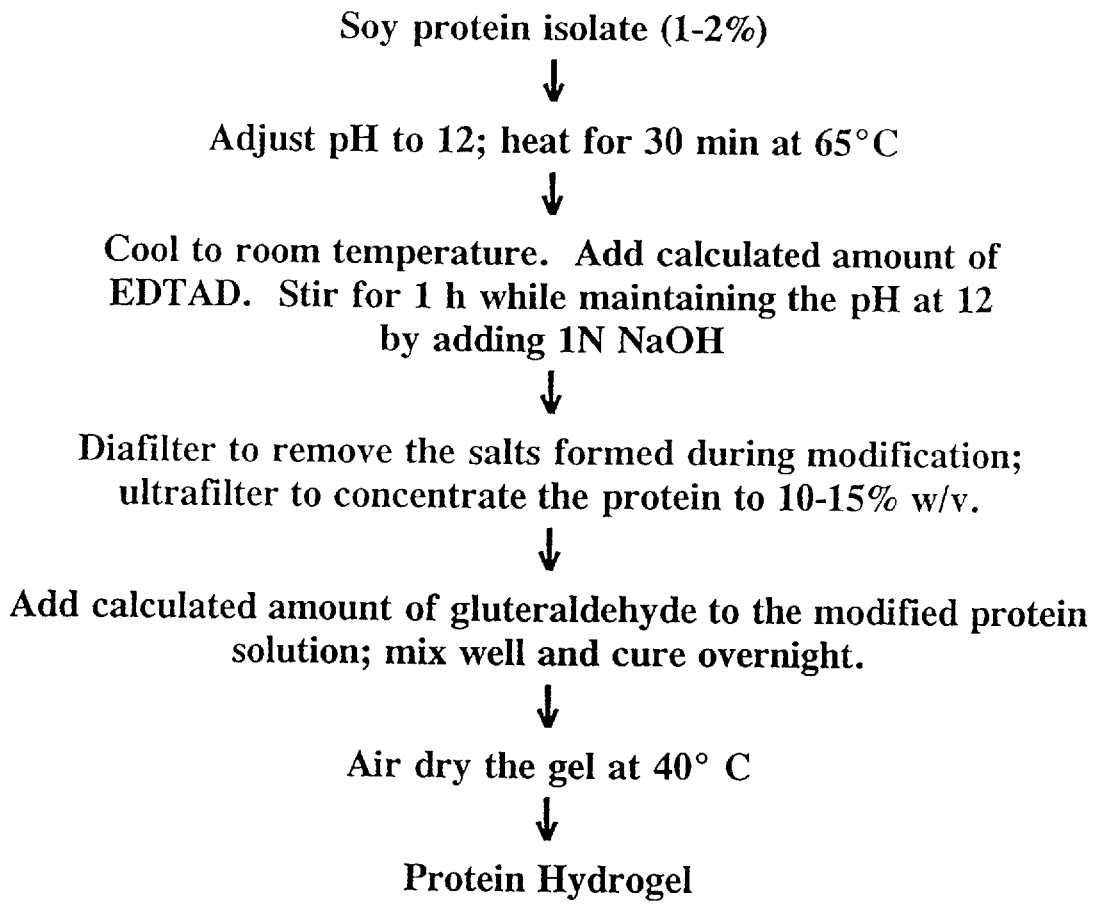
FIG. 10 is a flow chart depicting the preferred method of making a protein hydrogel according to the present invention.

FIG. 10 depicts a process flow chart of the preferred method of making the presently claimed protein hydrogel. Briefly, a 1–2% soy protein isolate solution is adjusted to pH 12, and incubated at 65° C. for 30 minutes. The solution is then cooled to room temperature, and EDTAD is slowly added to the solution. The pH of the solution is maintained constant at 12 by addition of NaOH. The solution is then filtered (for instance, by dialysis) and concentrated. Glutaraldehyde is then added to the solution to crosslink the protein chains. The hydrogel is then cured overnight, and dried at 40° C.

The following protocols are provided for illustrative purposes only to aid in a complete understanding of the claimed invention. It is understood that the examples do not limit the invention claimed herein in any manner.

Materials

Defatted soy flour is commercially available from many suppliers, including Central Soya, Fort Wayne, Ind., USA. Glutaraldehyde and trinitrobenzenesulfonic acid (TNBS) can be obtained from Sigma Chemical Co., St. Louis, Mo., USA. Ethylenediaminetetraacetic dianhydride (EDTAD) can be obtained from Aldrich Chemical Co., Milwaukee, Wis., USA.

Preparation of Soy Protein Isolate (SPI) and Protein Determination

Defatted soy flour was extracted with water at pH 8.0 at a flour to water ratio of 1:10. The solution was centrifuged and the supernatant adjusted to pH 4.5 with 2M HCl to precipitate the proteins. The precipitate was redissolved in water at pH 8, dialyzed against water (pH 8.0) overnight, and lyophilized to yield soy protein isolate (SPI).

Protein concentration was determined by the dry weight method. A weighted aliquot of protein stock solution in deionized water was dried to a constant weight at 105° C. in a vacuum oven. The protein content is then expressed as w/w %.

Acylation

Acylation of the SPI was performed by the step-wise addition of solid EDTAD to a 1% aqueous solution of the SPI at 65° C. The pH of the protein solution is kept constant during the acylation by adding 1 N NaOH with a pH-Stat (Fisher Scientific). The duration of the acylation is normally on the order of two to three hours.

Crosslinking

150 µl of a 25% aqueous solution of glutaraldehyde was added to 10 ml of a 15% (w/w) solution of the acylated protein at pH 9.0 The mixture was stirred thoroughly with a magnetic stirrer, and the resultant gel cured overnight at room temperature. The cured gel was then air dried in an oven at 40° C.

Determination of the Extent of Protein Modification

The extent of acylation is expressed as the percentage of the total number of lysyl residues modified. The lysine content of the unmodified SPI, and the acylated SPI was determined by the TNBS method described by Hall et al. (*Analyst*, 1973:98, 673), which is incorporated herein by reference for its teaching of protein modification analysis:

To 1 ml of 4% NaHCO₃ was added 0.8 ml of a solution containing less than 5 mg SPI, followed by the addition of 0.2 ml of TNBS solution (12.5 mg/ml). The mixture was incubated at 40° C. for 2 hours, and then 3.5 ml of concentrated HCl was added to the mixture. The tube was stoppered and kept at 110° C. for 3 hours, and then cooled. After cooling, the volume was made up to 10 ml with deionized water. The solution was extracted twice with anhydrous diethyl ether. The tube was unstoppered and heated to 40° C. to allow the residual ether to escape. The absorbance of the yellow ε-TNP lysine solution was then measured at 415 nm against a blank. The amount of lysyl residues in the acylated and unacylated SPI was then determined from a standard curve constructed using lysine.

Swelling Properties

The swelling properties of the subject protein hydrogels was analyzed in the following fashion:

A known amount of dry gel is placed in a preweighed filter pouch similar in appearance to a tea bag. The pouch is then heat sealed. A control pouch of the same weight, without any gel, is also sealed. Both pouches are then immersed in deionized water at pH 6.7 at room temperature for 24 hours. The pouches are then centrifuged at 214×g for 5 minutes. After centrifugation, both pouches are weighed. The wet weight of the gel is determined by subtracting the weight of the control pouch from that of the sample pouch. The two pouches are then dried at 100° C. to a constant weight and re-weighed to calculate the dry weight of the gel. From the wet and dry weight of the gel sample, the grams of water absorbed per gram of dry gel is determined.

It is understood that the present invention is not limited to the particular embodiment, reagents, steps, or methods described herein, but embraces all such forms thereof as come within the scope of the attached claims.

What is claimed is:

1. A protein hydrogel comprising a protein wherein lysyl residues within the protein are modified by addition of one or more carboxyl moieties thereto to yield an acylated protein by treating the protein with an acylating agent wherein said acylating agent is a tetracarboxylic acid dianhydride, and further wherein the acylated protein is crosslinked with a bifunctional crosslinking reagent wherein the crosslinking reagent is a dialdehyde.

2. The protein hydrogel according to claim 1, wherein said acylating agent is ethylenediaminetetraacetic acid dianhydride.

3. The protein hydrogel according to claim 1 wherein said bifunctional aldehyde is selected from the group consisting of

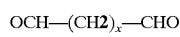

wherein X is an integer of from 2 to 8.

4. The protein hydrogel according to claim 3, wherein said bifunctional crosslinking agent is glutaraldehyde.

5. The protein hydrogel according to claim 1, wherein said protein comprises a protein derived from biomass.

6. The protein hydrogel according to claim 1, wherein said protein comprises a protein isolate derived from biomass.

7. The protein hydrogel according to claim 1, wherein said protein isolate is a soy bean protein isolate.

8. A protein hydrogel comprising:

a soy protein isolate, said soy protein isolate being acylated by treatment with ethylenediaminetetraacetic acid dianhydride to yield an acylated protein said acylated protein being crosslinked with glutaraldehyde.

* * * * *